(12) United States Patent
Furukawa et al.

(10) Patent No.: US 7,658,830 B2
(45) Date of Patent: Feb. 9, 2010

(54) CAPILLARY ARRAY AND ELECTROPHORESIS APPARATUS, AND METHODS

(75) Inventors: Takayasu Furukawa, Hitachinaka (JP); Nobuhiko Sato, Iruma (JP); Syozo Kasai, Hitachinaka (JP); Seiichi Ugai, Hitachinaka (JP); Motohiro Yamazaki, Hitachinaka (JP); Hiroyuki Tanaka, Hitachinaka (JP); Yuki Nonaka, Hitachinaka (JP); Yoshio Onodera, Hitachinaka (JP); Noriyuki Shimoda, Higashimurayama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 181 days.

(21) Appl. No.: 11/604,253

(22) Filed: Nov. 27, 2006

(65) Prior Publication Data
US 2007/0062814 A1  Mar. 22, 2007

Related U.S. Application Data

(63) Continuation of application No. 10/421,887, filed on Apr. 24, 2003, now Pat. No. 7,156,971.

(30) Foreign Application Priority Data
Apr. 26, 2002 (JP) .............................. 2002-125195

(51) Int. Cl.
    *G01N 27/453* (2006.01)
(52) U.S. Cl. ..................................... 204/601
(58) Field of Classification Search ......... 204/451–455, 204/601–605
    See application file for complete search history.

(56) References Cited

U.S. PATENT DOCUMENTS

| 5,198,091 | A | 3/1993 | Burolla et al. |
| 5,277,780 | A | 1/1994 | Kambara |
| 6,464,852 | B1 | 10/2002 | Gorfinkel et al. |
| 6,562,214 | B1 * | 5/2003 | Amrhein et al. ............. 204/601 |
| 2003/0146096 | A1 | 8/2003 | Cong et al. |

FOREIGN PATENT DOCUMENTS

| DE | 42 30 354 A1 | 3/1993 |
| EP | 0 490 406 A2 | 6/1992 |
| JP | 11-326276 A | 11/1999 |

(Continued)

OTHER PUBLICATIONS

JPO English language computer translation of Isomae et al. JP 2000-131278 A, patetn published on May 12, 2000.*

(Continued)

*Primary Examiner*—Alex Noguerola
(74) *Attorney, Agent, or Firm*—Dickstein Shapiro LLP (57) ABSTRACT

A capillary array capable of being easily mounted on an electrophoresis apparatus without damaging the capillaries. The capillary array can include a plurality of capillaries that can be fixed via hollow electrodes on a load header in a matrix arrangement. The load header can be disposed on the electrophoresis apparatus. The capillary array can include a capillary frame onto which a capillary head and a detection portion can be detachably mounted. The structure allows the load header, the capillary head, the detection unit and other portions of the capillary array to be handled as a unit, thereby making it easier to mount the capillary array on the electrophoresis apparatus.

7 Claims, 9 Drawing Sheets

FOREIGN PATENT DOCUMENTS

| | | | |
|---|---|---|---|
| JP | 2000-131278 A | * | 5/2000 |
| JP | 2001-324473 | | 11/2001 |
| WO | WO 98/14773 A | | 4/1998 |
| WO | WO 99/38005 A | | 7/1999 |
| WO | WO 00/16086 A | | 3/2000 |

OTHER PUBLICATIONS

JPO English-language computer translation of Mitsuru et al. (JP 11-326276 A).

* cited by examiner

CAPILLARY ARRAY AND ELECTROPHORESIS APPARATUS, AND METHODS

This is a continuation of application Ser. No. 10/421,887, filed Apr. 24, 2003, now U.S. Pat. No. 7,156,971, the entire disclosure of which is incorporated herein by reference.

BACKGROUND OF THE INVENTION

1. Field

The present teachings relate to a capillary-array electrophoresis apparatus for separating and analyzing samples, such as DNA or proteins. In particular, the present teachings relate to a capillary array.

2. Background Art

An example of a known capillary array electrophoresis apparatus is disclosed in Japanese Patent Publication (Unexamined Application) No. 2001-324473. The capillary array includes 16 capillaries each made of a quartz tube with an external diameter of about 0.35 mm and an inner diameter of about 0.05 mm. The capillary array has a load header on one end for injecting samples, and a capillary head on the other end for injecting a buffer solution

SUMMARY OF THE INVENTION

According to various embodiments, the present teachings provide a capillary array, an electrophoresis apparatus, and a method of mounting the capillary array onto the electrophoresis apparatus. The capillary array can include a frame onto which members attached to the capillaries, such as a load header, a capillary head, and a detection portion, can be detachably mounted. Because these members and the capillaries can be substantially handled as a unit, the capillary array can be relatively easily mounted on the electrophoresis apparatus. Because there is no need to handle the capillaries when coupling the load header to the electrophoresis apparatus, damage to the capillaries can be substantially prevented.

According to various embodiments, the present teachings provide a capillary array onto which members attached to the capillaries, such as a load header, a capillary head, and a detection portion, are mounted to a frame. This structure allows the capillaries to be spared from excessive load when a large amount of force is applied to the members fixed on the frame. As a result, damage to the capillaries, which are made of fragile material, such as glass, can be prevented. For example, the frame can be made of a flexible material such that a force applied to the members fixed to the frame through the capillaries can be absorbed by the frame, so that damage to the capillaries where they are connected to those members can be prevented.

According to various embodiments, the present teachings provide a capillary array including a frame onto which separators, for fastening capillaries without fixing them, are retained at predetermined positions. This structure allows the capillaries to be retained in the frame in substantially the same state as they are during electrophoresis. Further, since the capillaries are not fixed to the separators, the capillary array can be easily mounted on the electrophoresis apparatus. As a result, if a large amount of force is applied to the capillaries, the capillaries are not damaged where they contact with the separators.

According to various embodiments, the present teachings provide a method of mounting a capillary array on an electrophoresis apparatus by individually handling members attached to capillaries, such as a load header, a capillary head, and a detection unit. When a user handles two or more of the members simultaneously, there is a danger that a large amount of load will be applied to the capillaries, if they are pulled in different directions. Such danger can be avoided by the present teachings.

BRIEF DESCRIPTION OF THE DRAWINGS

The above and other objects, and features of the present teachings will be more particularly described with reference to the accompanying drawings, in which.

It is to be understood that both the foregoing general description and the following detailed description are exemplary and explanatory only, and are intended to provide an explanation of various embodiments of the present teachings.

DESCRIPTION OF THE INVENTION

Figure 2:
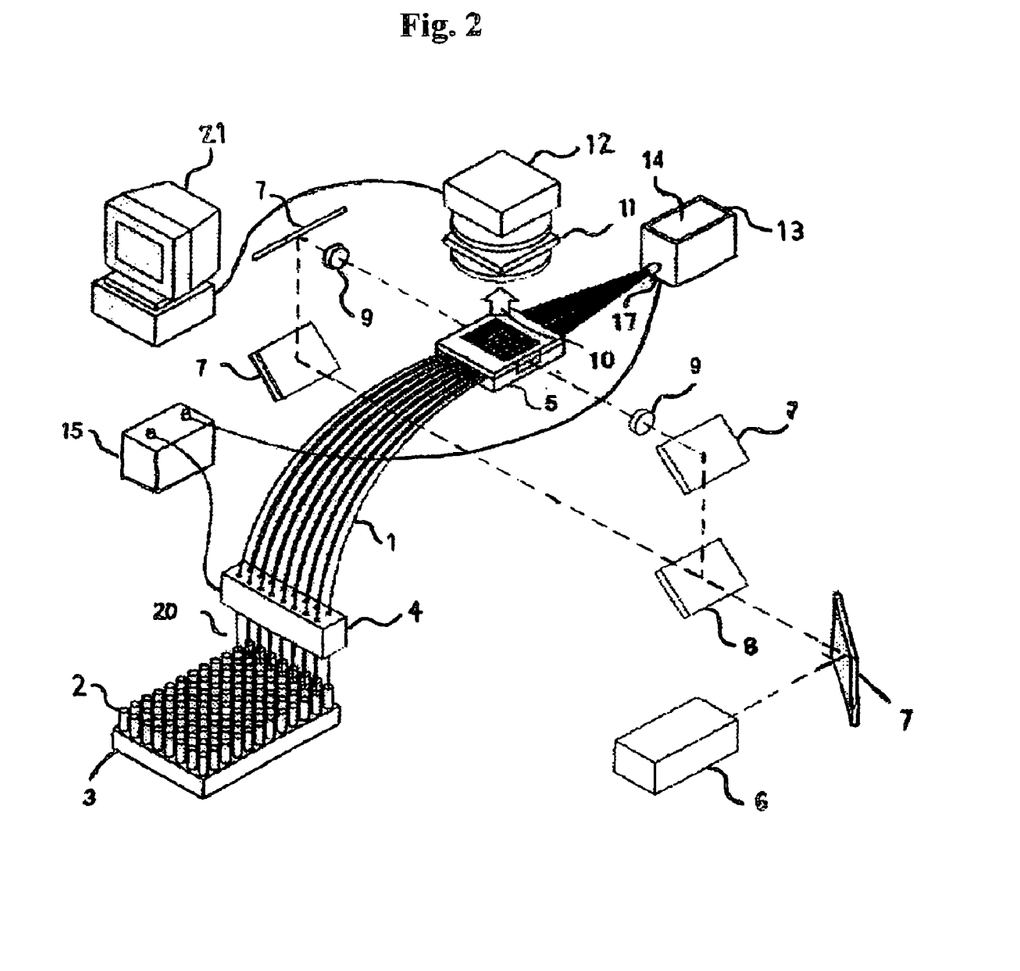
FIG. 2 schematically shows an electrophoresis apparatus according to various embodiments.

FIG. 2 schematically shows an electrophoresis apparatus including a capillary array according to various embodiments. A capillary array can include 96 capillaries 1. Each capillary 1 can be made, for example, of a quartz pipe, with an external diameter of about 0.15 mm and an inner diameter of about 0.05 mm, which can be, for example, resin-coated with polyimide.

According to various embodiments, the electrophoresis apparatus can include a load header 4 for feeding the capillaries with DNA from a sample tray 3 by electrophoresis. The sample tray 3 can store a number of sample containers 2 each containing about 10 µl or more of a fluorescent-labeled DNA sample. The electrophoresis apparatus can include a detection unit 5 for arranging and fixing the capillaries 1 in order by sample number in the load header 4, and an excitation optical system including a mirror 7, a beam splitter 8 and a focusing lens 9 for irradiating the detection portion with excitation light from a laser light source 6. The electrophoresis apparatus can also include a detection lens system 11 for detecting fluorescence 10 as an optical signal, and a CCD camera 12.

According to various embodiments, the capillary array containing DNA or proteins to be subjected to electrophoresis can be irradiated by the laser light source 6 from either side of the detection unit 5. The laser 6 can be focused by the lens-type action of the capillaries 1, such that all of the capillaries 1 can be irradiated by the excitation light. Fluorescence emitted by each capillary 1 can be detected by the detection optics. On the other side of the load header 4, a capillary head 17 can be disposed. The capillary head 17 can bundle and bond multiple capillaries 1 together, and can affix them in an airtight and sealed manner to a buffer-solution container 14 containing a buffer solution 13. A high voltage of approximately 15 kV can be applied between an electrode 20 mounted on the load header 4 and the buffer-solution container 14 by a high-voltage source 15, such that the samples in the sample containers 2 can be electrophoresed by the buffer solution introduced from the buffer-solution container 14 to the capillaries 1, thus separating the samples. The samples can arrive at the detection unit 5 ordered by size as a result of differences in resistance experienced by the DNA samples as they pass through a gel substantially entirely filling the capillaries 1.

According to various embodiments, fluorescence corresponding to the four nucleotides, specifically, adenine, guanine, cytosine, and thymine, that can be emitted from the fluorescent-labeled DNA samples, can be detected by the CCD camera 12. Such an optical signal can be obtained by irradiating the capillaries 1 arranged on an optical flat plane with tolerances of several microns, by way of excitation light entering from either side of the detection unit 5.

Figure 1:
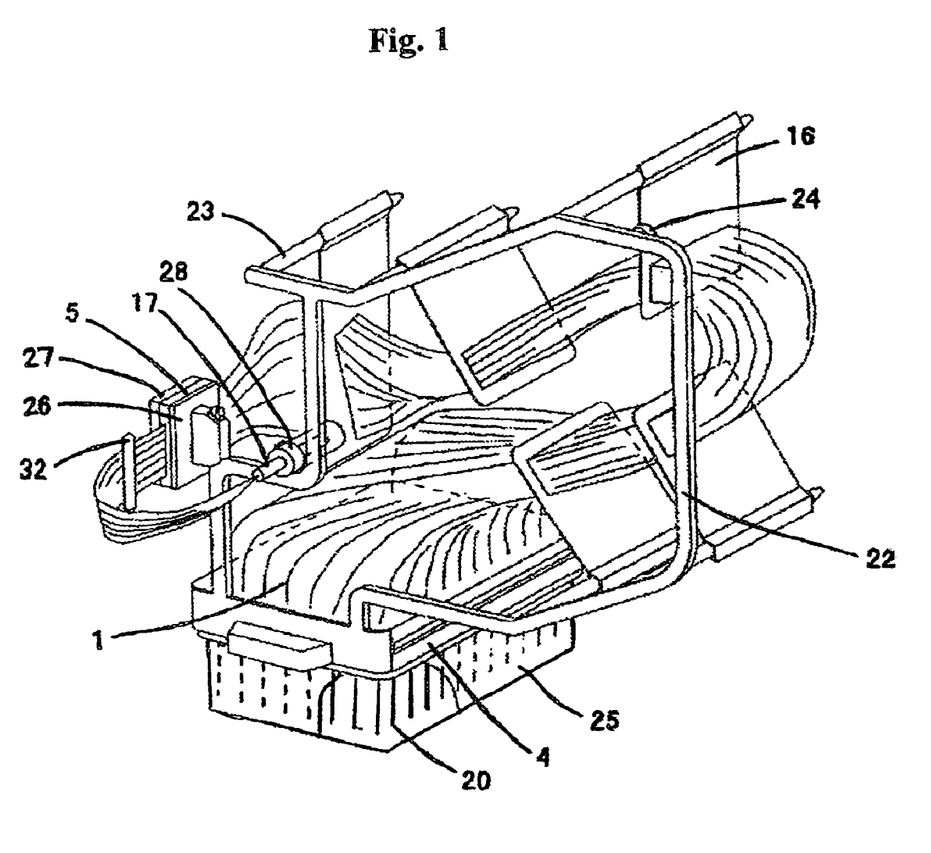
FIG. 1 is a perspective view of a capillary array according to various embodiments.

FIG. 1 shows a detailed view of the capillary array according to various embodiments, for facilitating the attachment or detachment of the capillaries 1 to the main body of electrophoresis apparatus. The capillary array can be a replaceable component that can be discarded after several months, or after several hundreds of times of use, when its separating capabilities are reduced. According to various embodiments, the capillary array can be composed of 96 capillaries 1, load header 4, separators 16, detection unit 5, capillary head 17, and a capillary frame 22 for holding the separators and other structure. A boss 24 can be attached to the capillary frame 22 for identifying the type of the capillary array being used.

According to various embodiments, the capillaries 1 can be made, for example, of quartz pipes having a diameter of about 0.15 mm. At the load header 4, the 96 capillaries 1 can be arranged in a matrix of eight rows and 12 columns via hollow electrodes 20. At the detection unit 5, the capillaries 1 can be arranged in parallel, and at the capillary head 17, they can be bundled and retained. Between the detection unit 5 and the load header 4, the capillaries can be loosened and retained by a series of separators 16. Between the detection unit 5 and the capillary head 17, the capillaries can be bundled into a strip by a thermo-compression sheet 32 to improve their rigidity.

The capillaries 1 can be bent into a three-dimensional shape such that they can extend vertically at the load header 4. Spaced intervals between the capillaries 1 can be substantially uniformly narrowed as the capillaries 1 extend away from the capillary head 17 and are bent. After extending for a certain distance, the capillaries 1 can be bent in the opposite direction in a more gradual curve and, after extending for another certain distance, they can be twisted in a clockwise direction by about 90 degrees, arranged in parallel in the detection portion, and then finally converged into one bundle by the load header 4. In this manner, the capillary array can be reduced in size, which in turn makes it possible to reduce the size of the thermostatic oven of the electrophoresis apparatus main body. As a result, the temperature in the thermostatic oven can be more easily controlled. If the capillaries 1 have different lengths, a certain positional relationship between the detection unit 5 and the load header 4 can be maintained, so that multiple kinds of capillary arrays with different capillary lengths can be employed in the electrophoresis apparatus.

According to various embodiments, the capillary frame 22 can be disposed near the path of the capillaries 1 and can be securely fitted with the load header 4 such that the frame 22 can be handled as an integral part of the load header 4. Further, the capillary frame 22 can detachably hold the detection unit 5 and the capillary head 17, and the separators 16 can be fixed to the frame via bars 23.

The capillary array can be mounted inside the thermostatic oven of the electrophoresis apparatus, and therefore, the capillary frame 22 can be made by injection-molding a plastic material with a breakdown voltage of 20 kV, and heat resistance of 70° C. or more. Any materials or production processes may be employed as long as they can produce components that can sustain the above conditions.

According to various embodiments, the capillary frame 22 can be flexible. If a rigid capillary frame were to be used, it could break if struck during handling, or if the weight of components mounted along the capillaries 1, were to be applied to the thin, wire-like capillaries. Thus, by providing the capillary frame 22 with flexibility, various external forces can be absorbed and the damage to the capillaries 1 can be substantially prevented.

Figure 3:
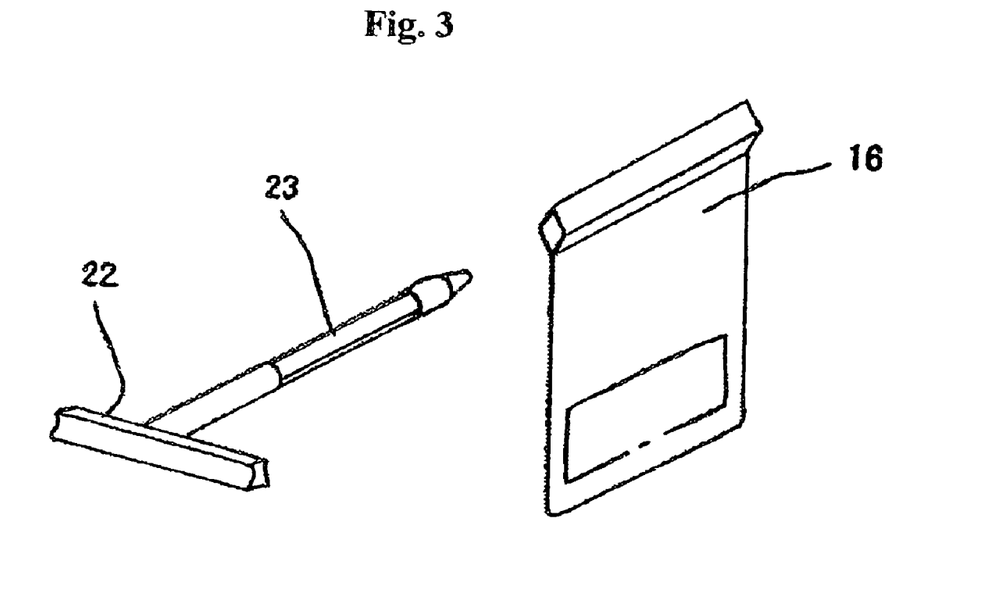
FIG. 3 is a perspective view showing a relationship between a separator and a bar according to various embodiments.

FIG. 3 is a perspective view of a separator 16 for orderly arranging the multiple capillaries 1 and a bar 23 for supporting the separator 16. The separator 16 can be retained by the capillary frame 22 via the bar 23 that can be attached to the capillary frame 22. The separator 16 can function to arrange the capillaries 1 in a matrix by fixing them in place one by one, such that they can extend from the load header 4 to the vicinity of the detection unit 5 without touching one another. The number of pairings of separators 16 and bars 23 can vary depending on the length of the capillaries 1, measured from about the center of the detection unit 5 to about the tip of the electrode 20 of the load header 4. For example, the number of pairings, can be 0, 3 and 5, for capillary lengths of about 220 mm, about 360 mm, and about 500 mm, respectively.

Figure 4:
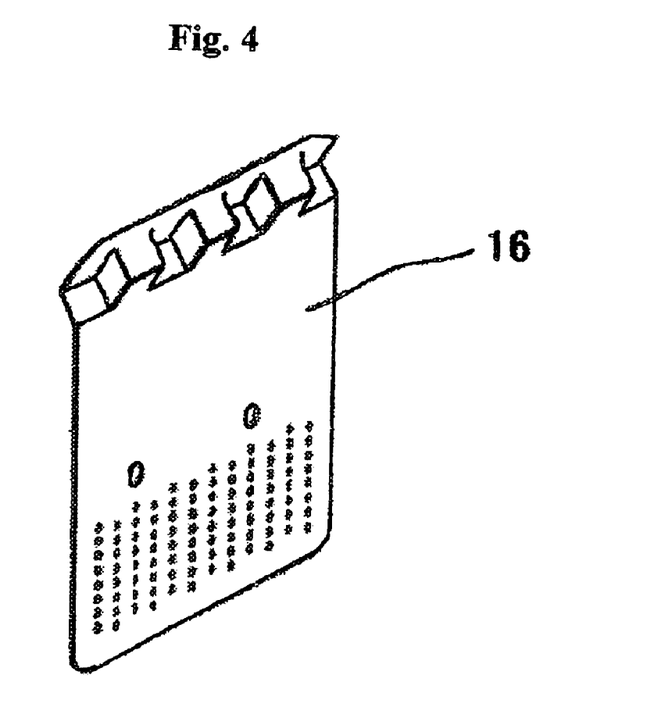
FIG. 4 is a perspective view of a separator according to various embodiments.

According to various embodiments, each of the separators 16 can be made of a thin plate, and they can be arranged in parallel to the flow of air inside the thermostatic oven, so that they do not block the airflow. FIG. 4 shows a separator 16 in more detail. The separator 16 can have 96 holes having about 1 mm diameters arranged in a cross-woven lattice of eight rows and 12 columns, for guiding the capillaries 1. For example, 96 capillaries 1 can be arranged by passing each one of them through a hole having a diameter of about 1 mm, without being fixed to the holes.

According to various embodiments, the capillaries 1 can be movable in a direction normal to the plane at the separator 16, so that the detection unit 5 and the capillary head 17 can be easily mounted on the electrophoresis apparatus without the capillaries' movement being interrupted by the separator 16. Further, even if a large amount of force is applied to the capillaries 1, the structure can absorb the force, preventing damage to the capillaries 1 when they contact the separator 16. When passing the 96 capillaries 1 through the individual separators 16 during assembly, the separators 16 can be stacked and handled as a single plate, thus facilitating the assembly of the capillary array. Specifically, each separator 16 can have two positioning holes for aligning the 96 holes of one separator with those of another when the separators are stacked.

According to various embodiments, each separator 16 can have a rhombic opening for engagement with a bar 23. The rhombic opening can be formed by alternately folding the plate in the shape of a mountain and a valley. Accordingly, each separator 16 can be shaped back into the original plate by extending the folds of the opening.

According to various embodiments, the bar 23 can include a square column portion whose sides can be substantially equal in length to each of the sides of the rhombic opening of the separator 16. As the bar 23 is squeezed into the rhombic opening of the separator 16, the square column of the bar 23 can forcibly turn the rhombus into a square, so that the bar 23 can be held tightly in the hole of the separator 16. The bar 23 can have a step between the circular column portion and the square column portion so that the bar 23 can be positioned axially, while the positioning of the bar 23 in its circumferential direction is determined by the square column portion. The tip of the bar 23 can be conically shaped so that it can be easily inserted into the separator 16, thus making its assembly easier.

According to various embodiments, the separator 16 that is closest to the detection unit 5 can be rotated by a little less than 90° with respect to those of the other separators 16, such that the capillaries 1 can be arranged in a single column at the detection unit 5.

Figure 5:
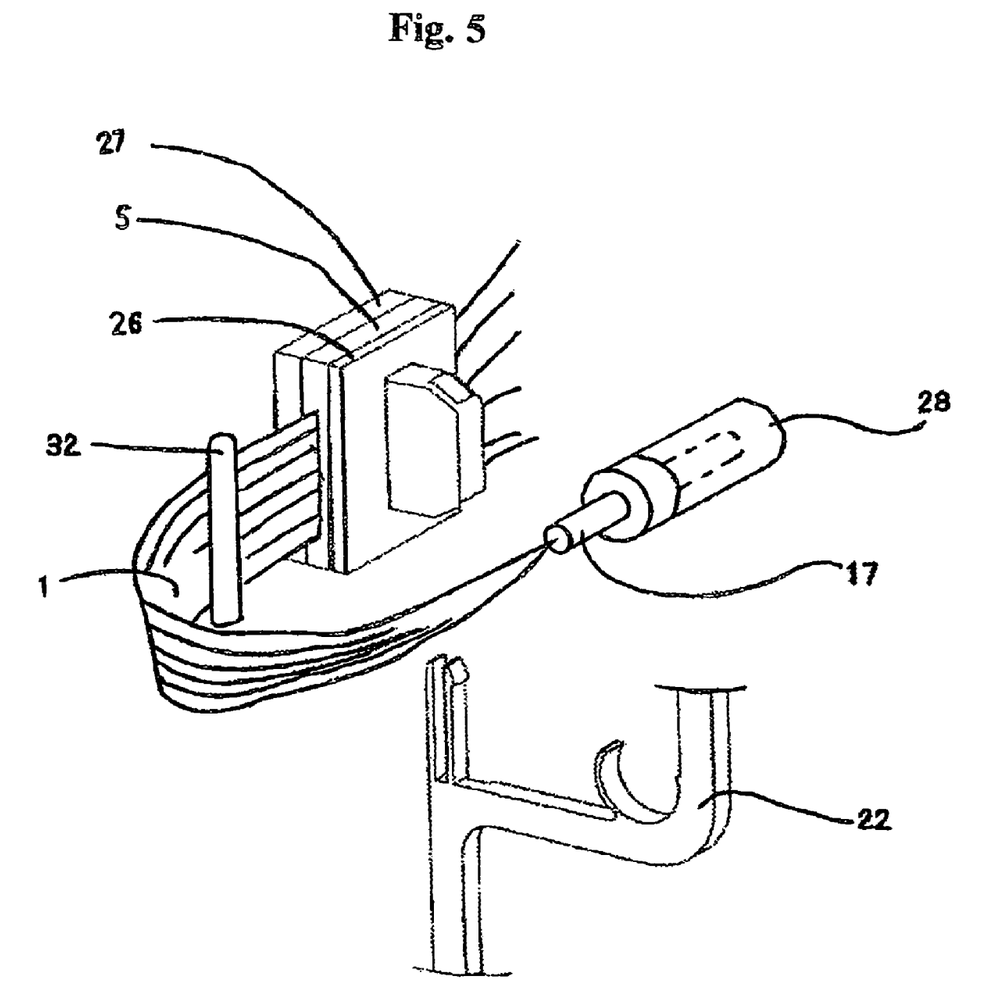
FIG. 5 is a perspective view showing a relationship among a capillary frame, a detection unit, and a capillary head according to various embodiments.

FIG. 5 is a perspective view of the capillary frame 22, the detection unit 5, and the capillary head 17.

According to various embodiments, when the capillary array is stored, or before it is mounted on the electrophoresis apparatus, the detection unit 5 can be positioned such that the capillaries 1 held by the separators 16 are not easily tangled or cluttered during the attachment of the detection unit 5 to the electrophoresis apparatus main body. Specifically, the detection unit 5 can be positioned, when stored, in approximately the same location as when it is mounted onto the electrophoresis apparatus. Because there is relatively little change in the three-dimensional shape of the capillaries 1 after mounting, any tangling or cluttering of the three-dimensional structure of the capillaries 1 that could be caused during transportation, or the like, can be fixed prior to mounting. As a result, the amount of adjustment required after the array is mounted on the apparatus can be reduced, and also the amount of work required to fix the capillaries 1 placed in the thermostatic oven, can be drastically reduced. As a result, damage to the capillaries 1 can be avoided.

During storage, the detection unit 5 can be protected by a cover 27 and a base 26, and can be retained by the capillary frame 22 via the base 26. The capillary head 17 can be inserted into a protection cap 28 which can be held by the capillary frame 22.

According to various embodiments, the capillary frame 22 can be secured to the load header 4, and the individual components can be held by the capillary frame 22. Because the relative positional relationship among the members secured to the capillaries 1, such as the load header 4, the detection unit 5 and the capillary head 17, can be fixed by the frame 22, the entire capillary array can be handled by way of the load header 4. Accordingly, even if a load were to be placed on the members secured to the capillaries 1, not much tension would be applied to the capillaries 1, thus substantially avoiding breakage or other damage.

In contrast, there would be a greater danger of breakage if the load header 4 and the detection unit 5 are both pulled, for example, in the case where the capillaries 1 are fixed and arranged on the load header 4 in a matrix, and are arranged at equal distances from the load header 4, in the detection unit 5. Greater danger of breakage would be present in such an arrangement because more tension could be applied to those capillaries 1 that are secured along the periphery of the matrix, particularly at the four corners of the matrix. Such kind of breakage can be avoided according to the various embodiments. Furthermore, as the capillary array can be handled with one hand, other operations, such as opening or closing the door of the apparatus, can be performed with the other hand. Thus, handling and workability during mounting and storage can be greatly improved.

As shown in FIG. 1, the capillary array can be stored without tipping or falling over, while the load header 4 can be protected by an electrode protection cap 25. The capillary head 17 can be protected by the capillary head protection cap 28, and the detection unit 5 can be protected by the base 26 and cover 27. The capillary array can be stably supported while the sample injection ends of the capillaries 1 are surrounded by the electrode protection cap 25, and the electrode protection cap 25 can be filled with buffer solution. The capillary array can be stored for a long period of time by wetting the sample injection ends of the capillaries 1 with the buffer solution to prevent the deterioration of the sample injection ends.

Figure 6A:
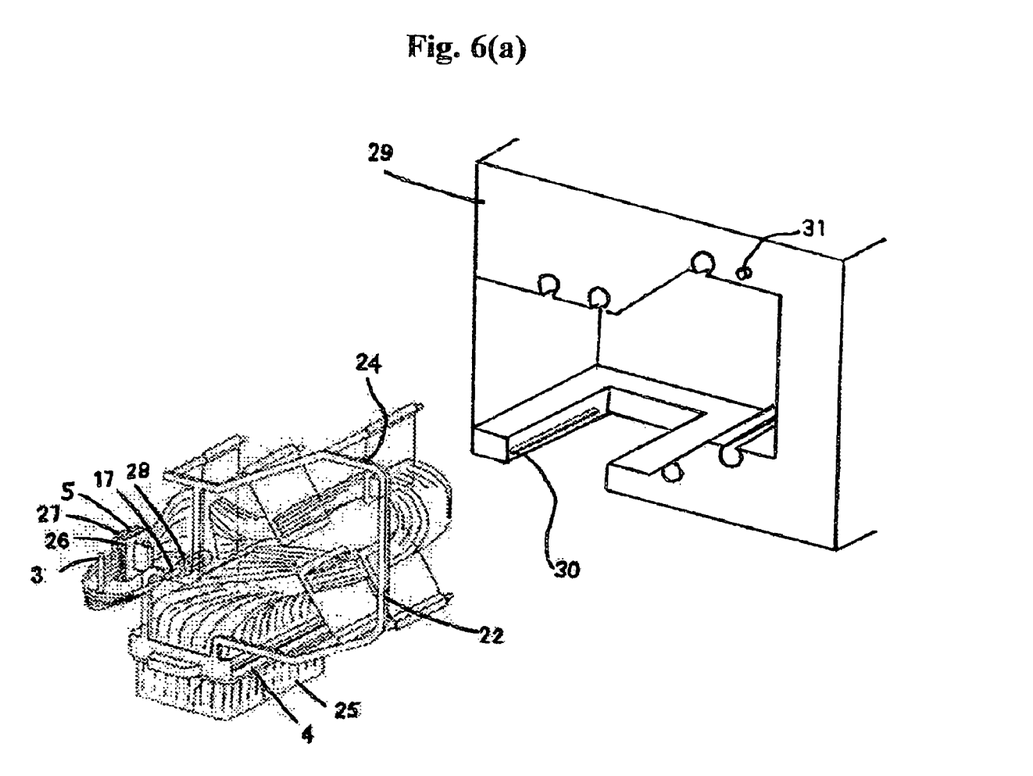
FIG. 6(a) is a perspective view showing a relationship between the electrophoresis apparatus and the capillary array according to various embodiments.
Figure 6B:
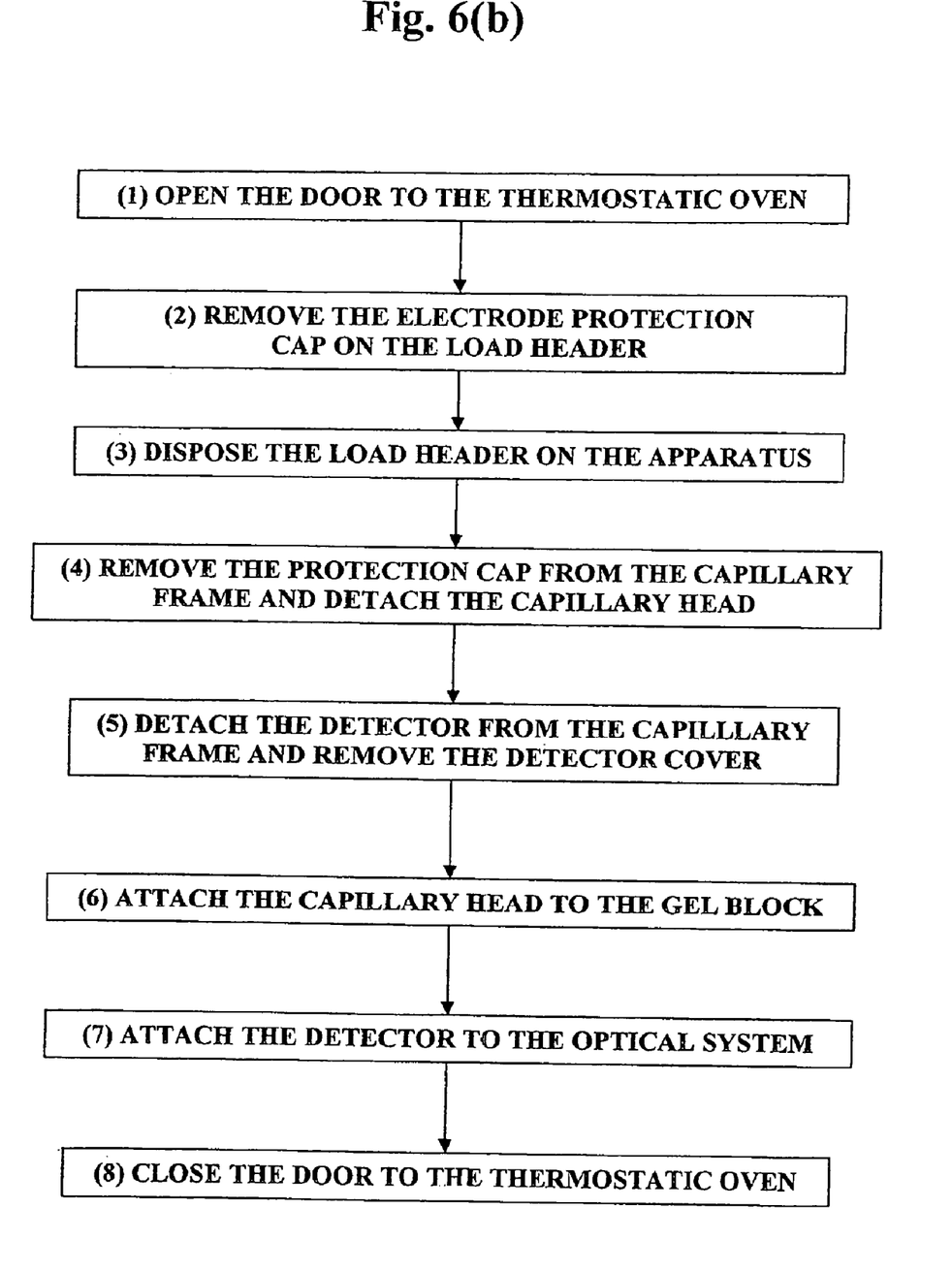
FIG. 6(b) shows a flow chart of a mounting operation in according to various embodiments.

FIG. 6(a) is a perspective view of the capillary array ready to be mounted in a thermostatic oven 29. FIG. 6(b) shows a flow chart of the mounting operation. Hereafter, the operation for attaching or detaching the capillary array will be described by referring to these drawings.

According to various embodiments, prior to the mounting operation, the individual components of the capillary array can be retained by the flexible capillary frame 22, and the capillaries 1 can be non-fixedly supported by the separators 16. Thus, the members attached to the capillaries 1 can be handled as a unit by holding the load header 4, while avoiding the danger of a large amount of tension being applied to the capillaries 1 during the operation.

First, the door to the thermostatic oven 29 can be opened, and the electrode protection cap 25 can be removed while holding the frontal sides of the load header 4. Then, a groove on either side of the load header 4 can be aligned with a guide 30 in the thermostatic oven 29 of the apparatus The capillary array can then be inserted into and mounted on the electrophoresis apparatus, while simultaneously inserting the bars 23 (which can range in number from 0 to 5) retaining the separators 16, into holes in the main body as guides. Because the capillary array can be inserted into the apparatus by holding the frontal sides of the load header 4, substantially no tension can be applied to the capillaries 1 during the insertion operation. While air is circulated from the back of the apparatus towards the front, to keep the temperature inside the thermostatic oven 29 constant, the influence of the capillary frame 22 on temperature control can be reduced because the frame 22 can be fixed on the load header 4 in a more downstream position of air flow than the capillaries 1. The frame's 22 influence on temperature control is further reduced because the capillary frame 22 is made of bar-like members that have substantially identical cross-sections and uniform thermal conductivity.

According to various embodiments, the capillary head protection cap 28 can be fitted to the capillary head 17, and can be removed from the capillary frame 22. The capillary head protection cap 28 can be removed from the capillary head 17. The detection unit 5 can be detached from the capillary frame 22 by holding a knob of the base 26 after removing the cover 27. The capillary head 17 and the detection unit 5 can be fixed on the apparatus in that order. Because the capillary head 17 and the detection unit 5 are retained by the capillary frame 22 in a position close to where they are to be connected to the apparatus, they can be connected to the apparatus without moving them over a long distance. Thus, danger of applying excessive tension to the capillaries 1 during the connecting operation can be substantially reduced.

The mounting operation can be completed by closing the door to the thermostatic oven 29. When it is desired to detach the capillary array from the electrophoresis apparatus, the above operation can be performed in the opposite sequence.

According to various embodiments, attachment of the separators 16 to the electrophoresis apparatus main body can be eliminated when mounting the capillary array. Thus, the 96 capillaries 1, having the predetermined three-dimensional shape, can be relatively easily disposed in the thermostatic oven 29. Previously, when an operator handled the multiple members attached to the capillaries 1 with two hands, there was a danger of breaking the capillaries 1 if the members were to be pulled away from one another. Such a danger of applying force to the individual members in opposite directions can be avoided in the present embodiment, because the load header 4, the capillary head 17, and the detection unit 5, are handled individually. Thus, the capillary array can be mounted on the apparatus even by a relatively unskilled operator.

As shown in FIG. 6(a), the capillary frame 22 can have a boss 24 for differentiating the type of the capillary array. According to various embodiments, the boss 24 can have an external size, for example, having about an 8 mm diameter about a 1.5 mm length, and its shape can vary depending on the characteristics of the capillary array. The apparatus can be equipped with a sensor 31 that is not influenced by high voltage during electrophoresis, and the boss 24 can be mounted at a corresponding position on the capillary frame 22. When the capillary array is mounted, the boss 24 can push the sensor 31 mounted on the apparatus, thereby providing an indication of the type of capillary array being mounted. While the sensor 31 of the apparatus is shown as a push-button switch, other types of sensors can be implemented according to various embodiments.

According to various embodiments, the capillary array can be easy to manufacture and assemble, can be easily mounted on the apparatus, and can reliably prevent damage to the capillaries 1 during handling.

Figure 7A:
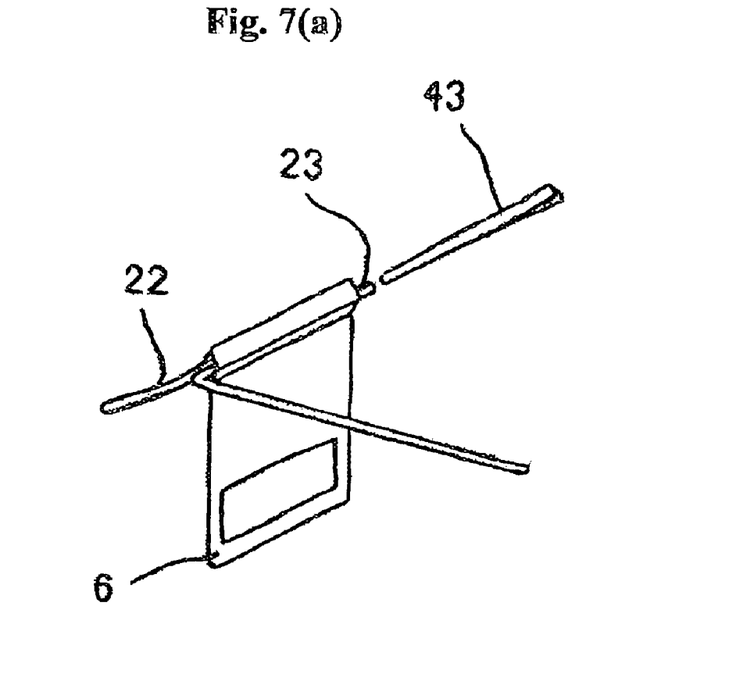
FIG. 7(a) is a perspective view of a separator during mounting operation according to various embodiments.
Figure 7B:
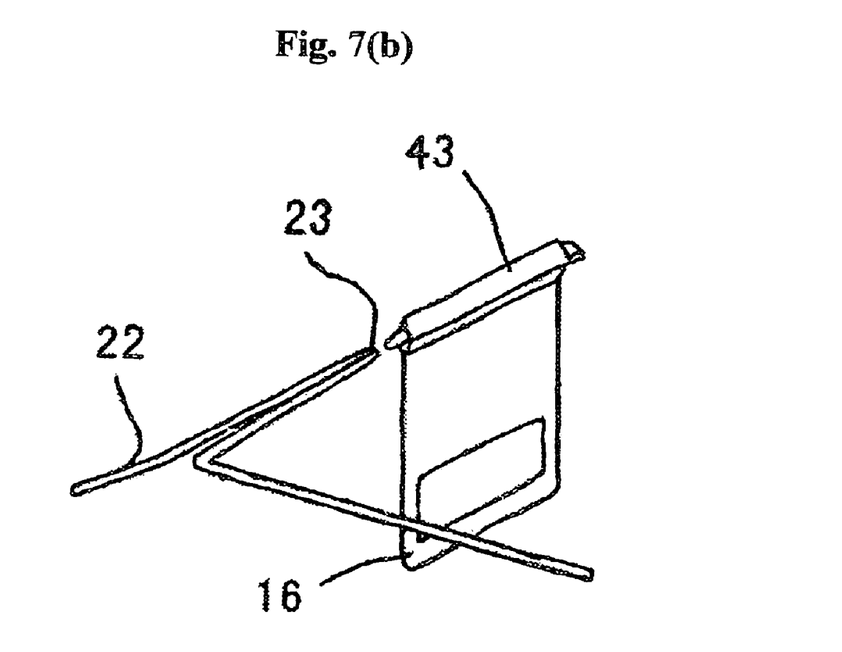
FIG. 7(b) is a perspective view of a separator during a mounting operation according to various embodiments.
Figure 8A:
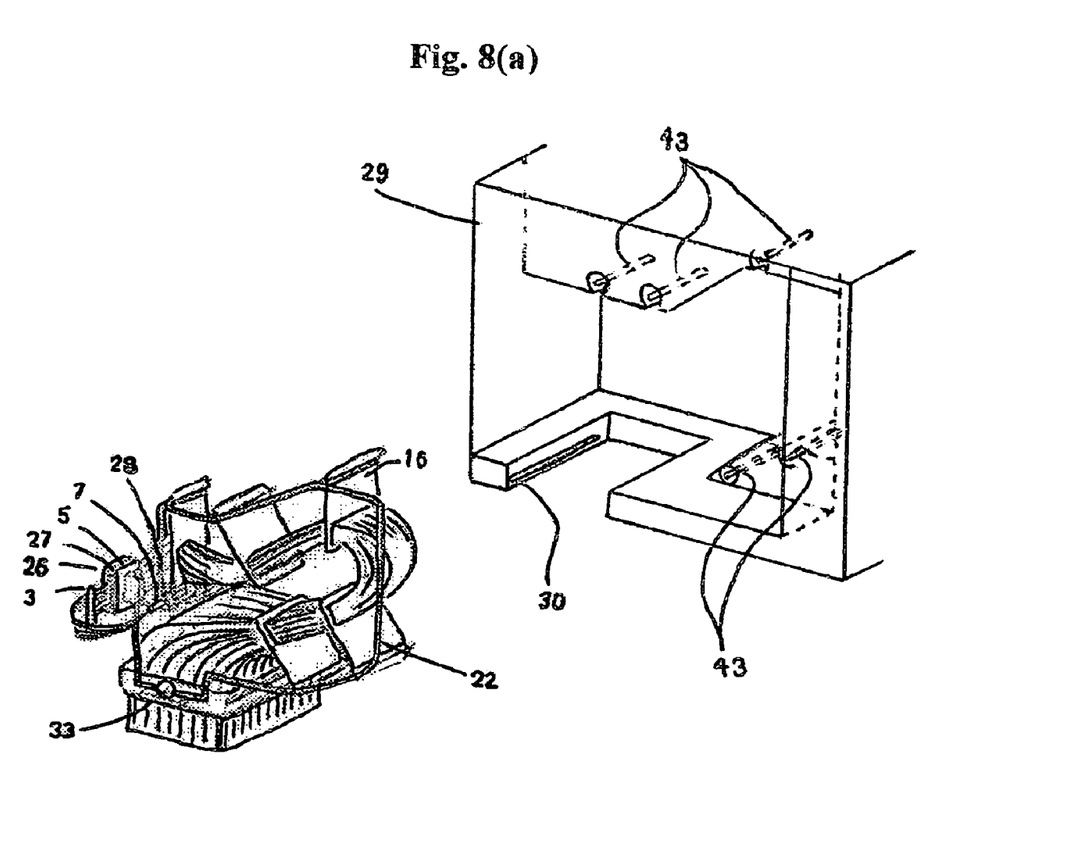
FIG. 8(a) is a perspective view showing a relationship between the electrophoresis apparatus and the capillary array according to various embodiments.
Figure 8B:
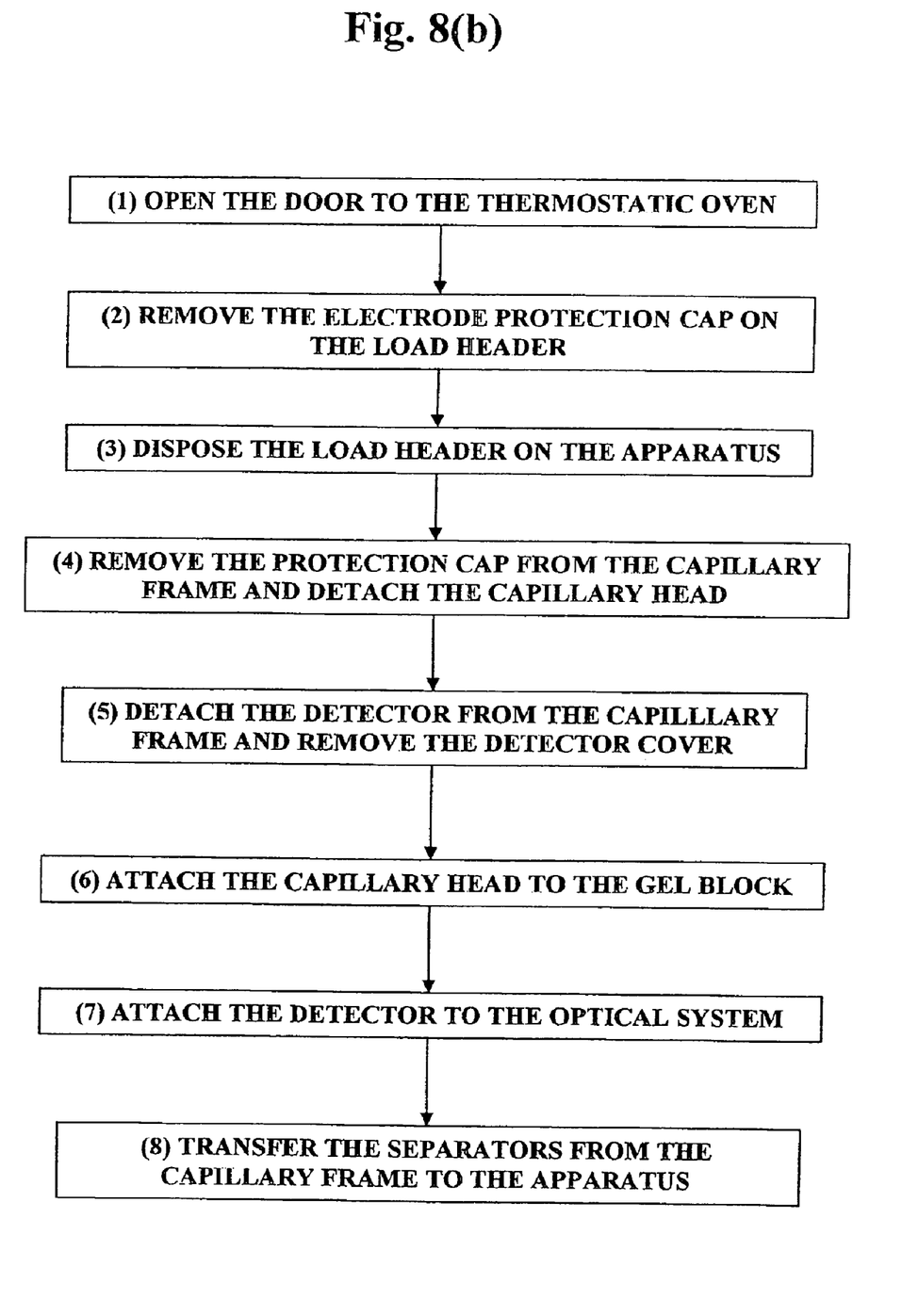
FIG. 8(b) shows a flow chart of a mounting operation according to various embodiments.

According to various embodiments, the capillary array can include separators 16 that are detachably retained by a metal capillary frame 22, and the capillary frame 22 can be removed from the capillary array during mounting. FIGS. 7(a) and 7(b) are perspective views showing the relationship between a separator 16 and a bar 43, as the separator 16 is handled. FIG. 8(a) is a perspective view of a capillary array about to be mounted. FIG. 8(b) shows a flow chart of the mounting operation. Differences between previous embodiments will be described by referring to FIGS. 7(a), 7(b), 8(a), and 8(b).

According to various embodiments, the capillary frame 22 can be made of stainless steel rod, and is capable of detachably retaining the separators 16, a detection unit 5, and a capillary head 17, by utilizing the rod's resilience. Because the stainless rod is more resilient than resins, and can be bent, the capillary frame 22 can be temporarily bent into a shape that allows the members carried by the frame 22, such as the detection unit 5, capillary head 17 and separators 16, to be easily detached or attached.

When mounting the capillary array of the various embodiments on the apparatus, the separators 16 retained by the frame 22 can be transferred to the apparatus. Thereafter, the capillary frame 22 can then be removed from the capillary array. The mounting operation will be described below, including the handling of the separators 16.

The sequence of operation is similar to that disclosed in previous embodiments up to the point where the detection unit 5 and the capillary head 17 are connected to the apparatus, after the load header 4 of the capillary head 17 is disposed in the thermostatic oven.

The bar 23 of the metal capillary frame 22 can be smaller than that disclosed in previous embodiments. Because the bar 23 retains the separator 16 during storage and mounting, and not after mounting. The apparatus has bars 43 for retaining the separators 16 when the capillary array is mounted in the electrophoresis apparatus.

When the load header 4 is slid onto the apparatus, the separators 16 can be positioned adjacent to the separator-retaining bars 43 on the electrophoresis apparatus, such that the bars 23 of the capillary frame 22 are aligned with the bars 43 on the apparatus. Because the bars 43 of the apparatus are situated at the tip of the bars 23 of the capillary frame 22, the separators 16 can be easily transferred to the bars 43 on the electrophoresis apparatus, by holding and sliding them one by one onto the apparatus. After all of the separators 16 are transferred, the capillary frame 22 can be removed from the load header 4, and the door to the thermostatic oven can then be closed, completing the mounting operation.

When the capillary array is to be detached from the apparatus, the above operation is performed in the opposite sequence.

Alternatively, the electrophoresis apparatus may be provided with angular openings adapted to fit with the rhombus openings of the separators 16, so that, when the load header 4 is disposed on the electrophoresis apparatus, the rhombus openings of the separators 16 can be inserted into and fitted with the openings. In this way, the separators 16 can be easily attached to the apparatus.

Although the present embodiment transfers the separators 16 between the capillary frame 22 and the electrophoresis apparatus, the capillary array can be easily mounted on the electrophoresis apparatus while preventing damage to the capillaries during the handling of the capillary array. Further, the productivity of the capillary array can be improved.

The present teachings make it easier to mount the capillary array on the electrophoresis apparatus. The present teachings also help prevent damage to the capillaries during handling of the capillary array, and allow the productivity of the capillary array to be improved.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. A capillary array comprising:
a plurality of capillaries each having a first end and a second end, the plurality of capillaries being filled with a polymer capable of separating samples;
a capillary head arranged to retain the first ends of the plurality of capillaries, and capable of being connected to an electrophoresis apparatus;
a load header arranged to retain the second ends of the plurality of the capillaries at a predetermined position, and capable of being connected to an electrophoresis apparatus;
a detection unit arranged to retain the capillaries at least at a predetermined position;
one or more separators individually supporting the capillaries; and a frame capable of supporting the load header, the capillary head, the detection unit, and the one or more separators, wherein the frame is flexible and the frame supporting the load header, the capillary head, the detection unit, and the one or more separators can be mounted to the main body of the electrophoresis apparatus.

2. The capillary array according to claim 1, wherein the capillaries are twisted by one of the one or more separators.

3. The capillary array according to claim 1, wherein the capillaries are twisted at an angle of about 90 degrees by one of the one or more separators.

4. The capillary array according to claim 1, wherein the one or more separators are arranged to hold but not to fix the capillaries.

5. The capillary array according to claim 1, wherein the one or more separators are arranged to be detachable from the frame.

6. The capillary array according to claim 1, wherein the load header, the capillary head, and the detection unit are arranged to be detachable from the frame.

7. A capillary array comprising:
a plurality of capillaries each having a first end and a second end, the plurality of capillaries being filled with a polymer capable of separating samples;
a capillary head arranged to retain the first ends of the plurality of capillaries, and capable of being connected to an electrophoresis apparatus;
a load header arranged to retain the second ends of the plurality of the capillaries at a predetermined position, and capable of being connected to an electrophoresis apparatus;
a detection unit arranged to retain the capillaries at least at a predetermined position;
one or more separators arranged to individually support the capillaries so that air can be circulated between the capillaries for heat dissipation; and
a frame capable of supporting the load header, the capillary head, the detection unit, and the one or more separators.

* * * * *

UNITED STATES PATENT AND TRADEMARK OFFICE
CERTIFICATE OF CORRECTION

| | | |
|---|---|---|
| PATENT NO. | : 7,658,830 B2 | Page 1 of 1 |
| APPLICATION NO. | : 11/604253 | |
| DATED | : February 9, 2010 | |
| INVENTOR(S) | : Takayasu Furukawa et al. | |

It is certified that error appears in the above-identified patent and that said Letters Patent is hereby corrected as shown below:

Title Page, Item no. [45], change "Date of Patent: Feb. 9, 2010" to
--**Date of Patent: * Feb. 9, 2010**--.

Item (*) Notice, change "Notice: Subject to any disclaimer, the term of this patent is extended or adjusted under 35 U.S.C. 154(b) by 181 days" to --Notice: Subject to any disclaimer, the term of this patent is extended or adjusted under 35 U.S.C. 154(b) by 181 days. This patent is subject to a terminal disclaimer.--.

Signed and Sealed this

Twenty-fifth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,658,830 B2 Page 1 of 1
APPLICATION NO. : 11/604253
DATED : February 9, 2010
INVENTOR(S) : Furukawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 255 days.

Signed and Sealed this

Twenty-eighth Day of December, 2010

David J. Kappos
*Director of the United States Patent and Trademark Office*